US005286258A

United States Patent [19]
Haber et al.

[11] Patent Number: 5,286,258
[45] Date of Patent: * Feb. 15, 1994

[54] MULTIPHARMACEUTICAL DELIVERY SYSTEM

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[*] Notice: The portion of the term of this patent subsequent to Sep. 15, 2009 has been disclaimed.

[21] Appl. No.: 668,278

[22] Filed: Mar. 8, 1991

[51] Int. Cl.$^5$ .............................................. A61M 37/00
[52] U.S. Cl. ..................................... 604/90; 604/191; 604/199; 604/236; 604/240; 604/247; 604/248; 604/416; 206/219; 222/136
[58] Field of Search ....................... 604/30, 34, 80, 82, 604/83, 85, 87, 89, 90, 187, 198, 216, 218, 236, 237, 247, 191, 199, 240, 416, 248; 137/844, 845, 846, 849; 206/221, 219; 222/130, 135–137, 129, 145

[56] References Cited

U.S. PATENT DOCUMENTS

| | | | |
|---|---|---|---|
| 595,942 | 12/1897 | Diehl et al. | 222/135 |
| 2,515,110 | 7/1950 | Bornstein | 137/846 |
| 3,489,147 | 1/1970 | Shaw | 222/137 |
| 3,767,085 | 10/1973 | Cannon et al. | 222/137 |
| 3,814,289 | 6/1974 | Robbins | 222/135 |
| 4,044,757 | 8/1977 | McWhorter et al. | 604/82 |
| 4,109,653 | 8/1978 | Kozam et al. | 604/191 |
| 4,381,778 | 5/1983 | Kozam et al. | 604/249 |
| 4,386,717 | 6/1983 | Koob | 222/136 |
| 4,610,666 | 9/1986 | Pizzino | 604/249 |
| 4,631,055 | 12/1986 | Redl et al. | 604/82 |
| 4,666,430 | 5/1987 | Brown et al. | 604/249 |
| 4,673,296 | 6/1987 | Sjogren | 222/137 |
| 4,795,441 | 1/1989 | Bhatt | 604/124 |
| 4,846,405 | 7/1989 | Zimmermann | 604/83 |
| 4,874,368 | 10/1989 | Miller et al. | 604/82 |
| 4,915,688 | 4/1990 | Bischof et al. | 604/83 |
| 5,019,048 | 5/1991 | Margolin | 604/204 |
| 5,067,948 | 11/1991 | Haber et al. | 604/213 |
| 5,147,323 | 9/1992 | Haber et al. | 604/205 |

FOREIGN PATENT DOCUMENTS 1815118 6/1970 Fed. Rep. of Germany.
0848204 9/1960 United Kingdom.

Primary Examiner—John D. Yasko
Assistant Examiner—Mark Bockelman
Attorney, Agent, or Firm—Townsend and Townsend Khourie and Crew

[57] ABSTRACT

A multipharmaceutical delivery system, such as a syringe (2) or a topical pharmaceutical applicator, suitable for a simultaneous delivery of a mixture (124) of two or more mixed pharmaceuticals (52, 120) in selected amounts and proportions, includes a body (4, 180) with first and second variable volume reservoirs (24, 26), containing the first and second liquids or other flowable materials, such as creams and salves. The reservoirs are connected to a variable volume accumulator chamber (31) through check valves (28) to permit liquid to flow from the reservoirs into the accumulator chamber but not the reverse. A delivery head, such as a needle assembly (78) or a spray nozzle assembly (196), is selectively fluidly coupled to the accumulator chamber by an exit path (106, 202) formed in the body. After the two liquids are driven into the accumulator chamber, typically one liquid at a time, the delivery head is fluidly coupled to the accumulator chamber and the accumulator piston (30) is actuated, thus forcing the liquid mixture from the accumulator chamber, through the exit path and through the delivery head during an injection or other application of the mixture.

24 Claims, 14 Drawing Sheets

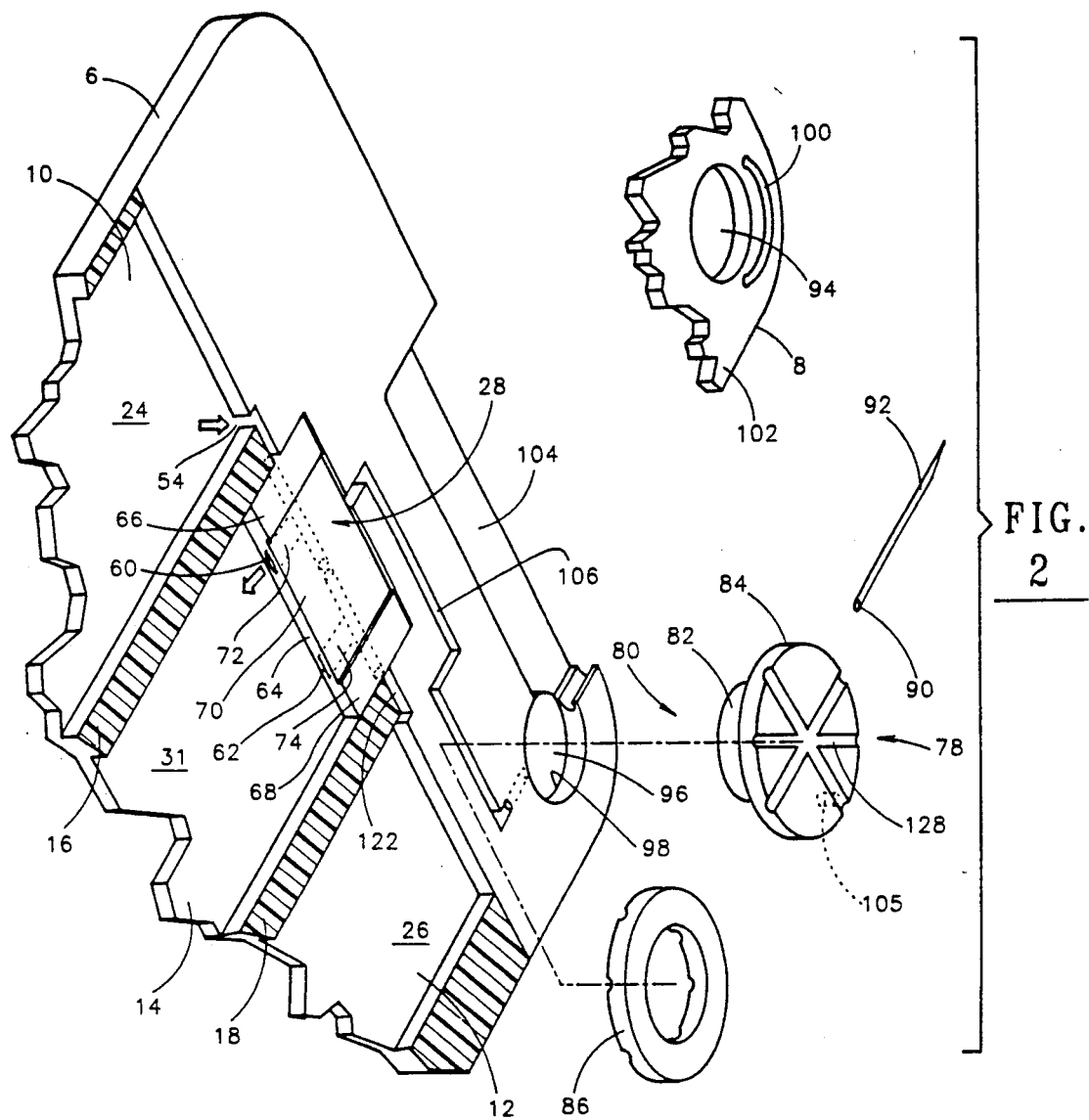
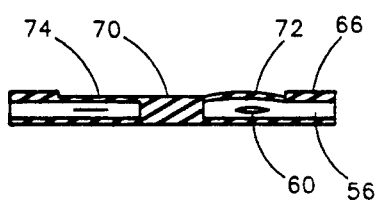
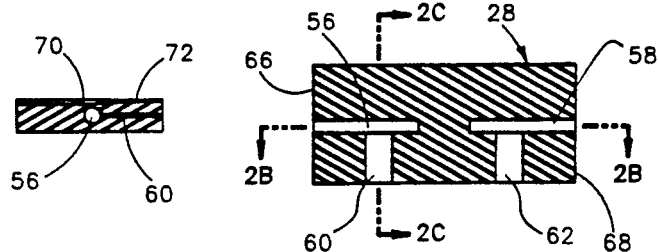
FIG. 2
FIG. 2B
FIG. 2C
FIG. 2A

MULTIPHARMACEUTICAL DELIVERY SYSTEM

CROSS REFERENCE TO RELATED APPLICATIONS

This is related to U.S. patent application Ser. No. 07/667,319 now U.S. Pat. No. 5,147,323, titled MULTIPLE CARTRIDGE SYRINGE, filed on the same day as this application, the disclosure of which is incorporated by reference.

BACKGROUND OF THE INVENTION

Therapeutic insulin is of three basic types: fast-acting, intermediate-acting and long-acting. Insulin users often use a combination of two types of insulin depending on the user's blood sugar level, the time of day, nourishment intake and expected activity. For example, insulin injected at the beginning of an active day may have more of the fast-acting insulin, while the insulin injection given at the end of the day before going to bed would likely have more intermediate- or long-acting insulin.

One of the problems with conventional insulin syringes is that they are designed to inject only one type of insulin, not a combination. Although insulin can be obtained as a mixture of the two types, the mixtures are generally a set combination, such as 70% intermediate-acting and 30% fast-acting. Thus, the prior art limits the insulin user to a preset mixture of the two insulins or the need to make two separate injections.

SUMMARY OF THE INVENTION

The present invention is directed to a variable ratio multipharmaceutical delivery system, typically in the form of a syringe, suitable for the simultaneous delivery of two or more mixed flowable pharmaceuticals in selected amounts and proportions. The delivery system includes first and second variable volume reservoirs, containing the first and second pharmaceuticals, and a variable volume accumulator chamber. The reservoirs and accumulator chamber are preferably formed within a common body. The reservoirs are preferably connected to the accumulator chamber through check valves to permit fluid flow from the reservoirs into the accumulator chamber but not the reverse. The delivery system also includes a delivery head, typically a hollow needle assembly, selectively fluidly coupled to the accumulator chamber. After the two pharmaceuticals are driven from the reservoirs and into the accumulator chamber, typically one pharmaceutical at a time, the delivery head is fluidly coupled to the accumulator chamber and the mixture is forced from the accumulator chamber and through the delivery head to permit administration of the mixture, typically by injection.

One of the key features of the invention is that the first and second reservoirs and the accumulator chamber can be made as integral parts of the delivery system. By making the reservoirs and the accumulator chamber with a low-profile, preferably elliptical, configuration, the delivery system can be easily carried in one's pocket or purse while holding, for example, sufficient insulin for several injections. Another advantage of the invention is that, prior to a first injection, and after each injection, the accumulator piston is positioned fully within the accumulator chamber to permit the stem to be fully housed within the accumulator chamber region.

With the delivery system configured as a flat, rectangular product, reminiscent of a credit card, the delivery system is easy to grasp and, when configured as a syringe, quite suitable for self-injection usage using one hand. When used as a self-injection syringe for insulin users, the invention reduces or eliminates the stigma of abnormality often created by the use of conventional syringes.

Another aspect of the invention is the use of a novel elastomeric valve block which functions as a check valve. The valve block prevents liquid from flowing back into either the first or second reservoirs in a simplistic and economical manner.

The invention is described with the first and second reservoirs and the accumulator chamber created using piston and cylinder arrangements. However, other variable volume structures, such as flexible bags in which the volume can be reduced by squeezing or other manipulation, can be used instead. Also, for enhanced sterility, a flexible tubular skirt can be connected to the accumulator piston at one end and to the proximal end of the accumulator chamber at the other.

The invention, in one preferred embodiment, is configured as a syringe using a hollow needle assembly as the delivery head. However, the invention can be practiced using needle-less injectors as well. The delivery head can also be configured as a topical applicator using rollers or sprayers to apply a liquid pharmaceutical directly onto the patient's skin or indirectly onto a bandage or patch, such bandage or patch being applied to the patient's skin. Spray-type delivery heads can be configured for use as an inhaler as well.

Other features and advantages of the invention will appear from the following description in which the preferred embodiments have been set forth in detail in conjunction with the accompanying drawings.

BRIEF DESCRIPTION OF THE DRAWINGS

FIG. 2 is an enlarged, partially exploded isometric view of a portion of the syringe of FIG. 1;

FIGS. 2A, 2B and 2C are separate cross-sectional views of the valve body of FIG. 2;

DESCRIPTION OF THE PREFERRED EMBODIMENTS

Figure 1:
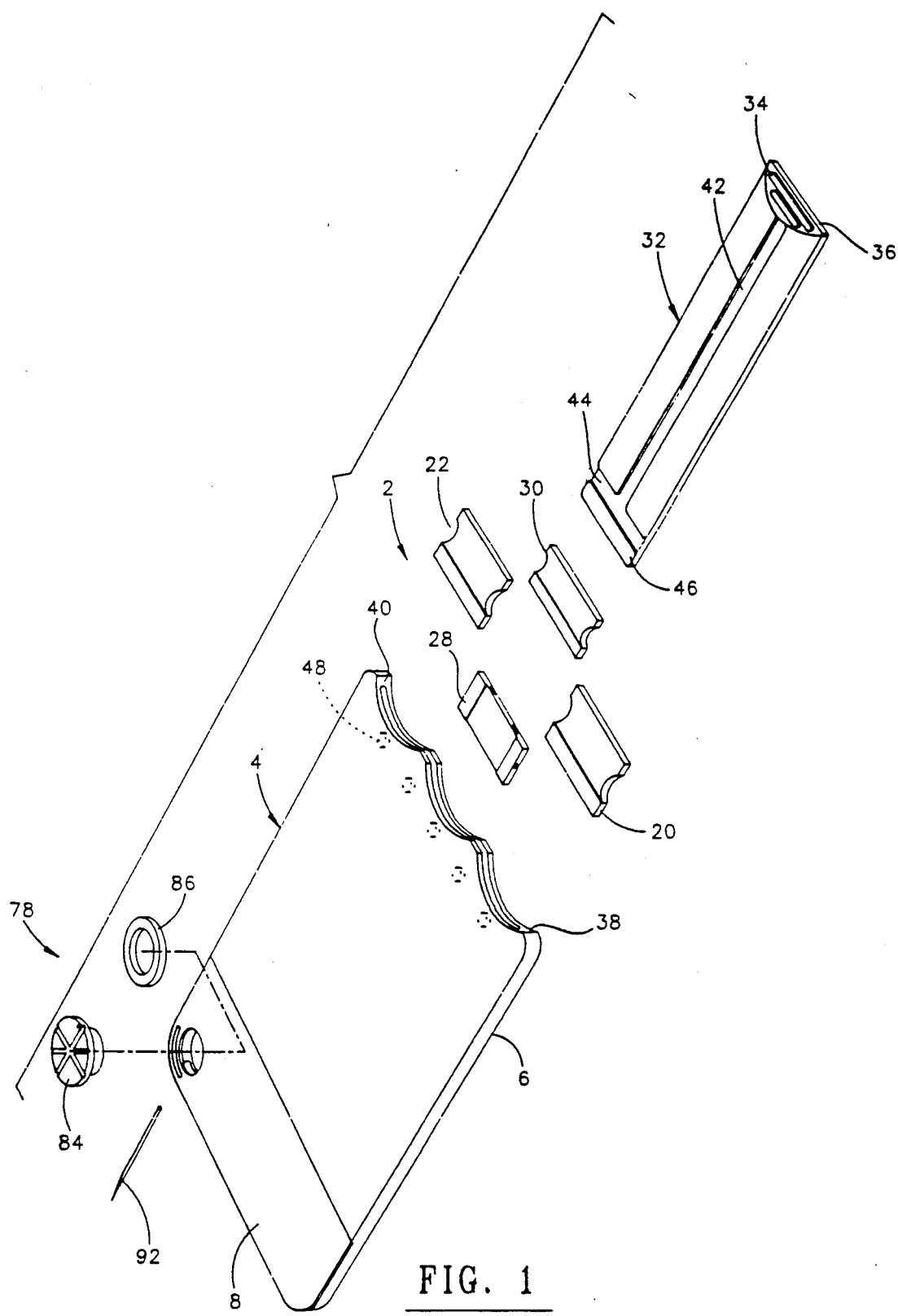
FIG. 1 is a partially exploded isometric view of a multipharmaceutical syringe made according to the invention.
Figure 3:
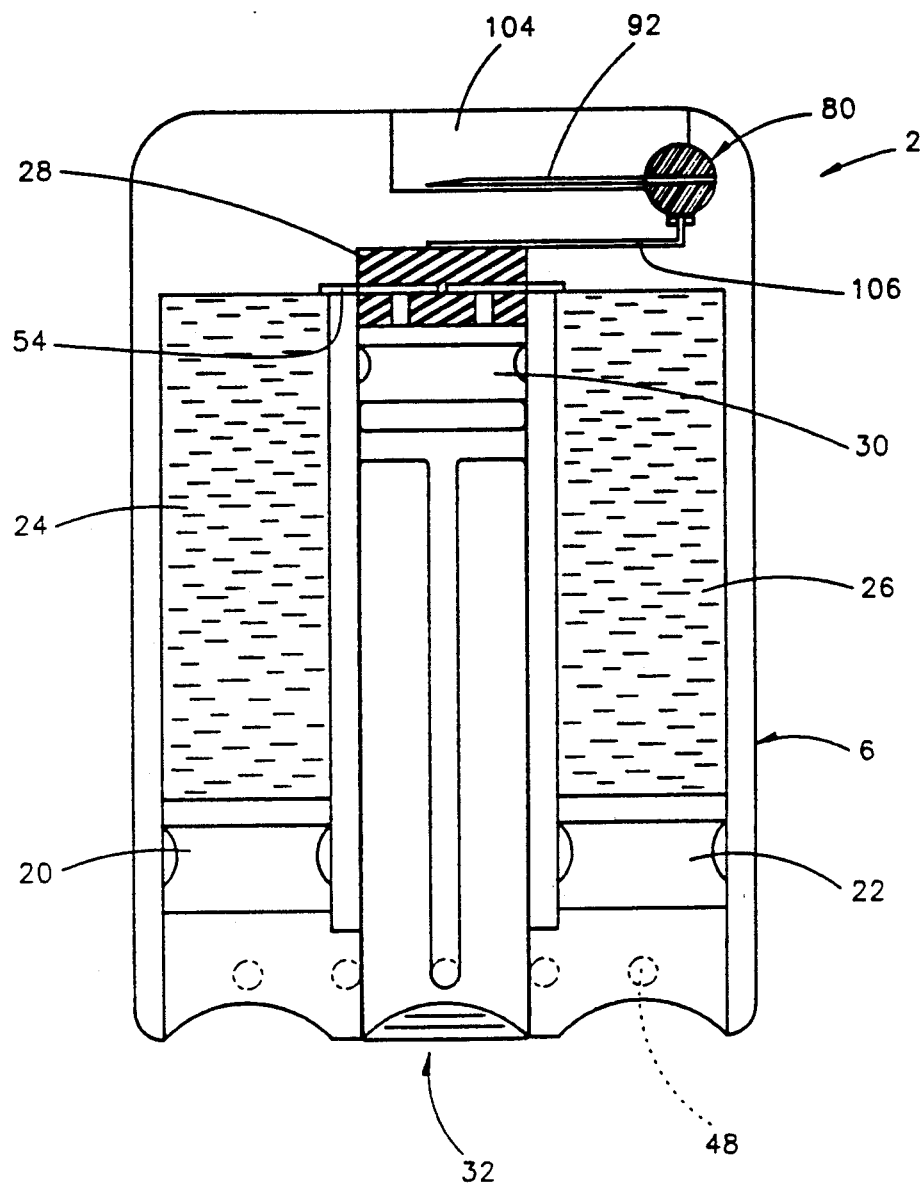
FIG. 3 is a plan view of a syringe of FIG. 1 shown with the cover removed, with portions of the base broken away for clarity, and in its initial, as-shipped condition.

Referring the reader to FIGS. 1-3, a multipharmaceutical syringe 2, especially useful for dispensing insulin, includes a body 4 made up of a base 6 and a cover 8. Base 6 and cover 8 are preferably made of clear, pharmaceutically compatible plastic, such as polypropylene or acrylic, and are joined, such as by ultrasonic welding techniques or using suitable adhesive. Base 6 has three elongate, flattened elliptical cutouts 10, 12, 14 separated by walls 16, 18. First and second pistons 20, 22 are slidably mounted within cutouts 10, 12 and define first and second variable volume reservoirs 24, 26. A valve body 28 is mounted in a cutout 27 formed in base 6 at the distal end of elongate cutout 14 for the reasons to be discussed below. An accumulator piston 30 is slidably mounted within cutout 14 to define a variable volume accumulator chamber 31 bounded by base 6, valve body 28, body supports 33 formed at the distal end of cutout 14 and accumulator piston 30. Pistons 20, 22 and 30 can each be made from one piece of an elastomeric material, such as silicone rubber. If desired, pistons 20, 22 and 30 can be multi-component parts having a leading edge of a resilient material, to provide a good seal, and a trailing edge of a low friction material, to provide guidance to keep the pistons from skewing within their respective cutouts.

Figure 12:
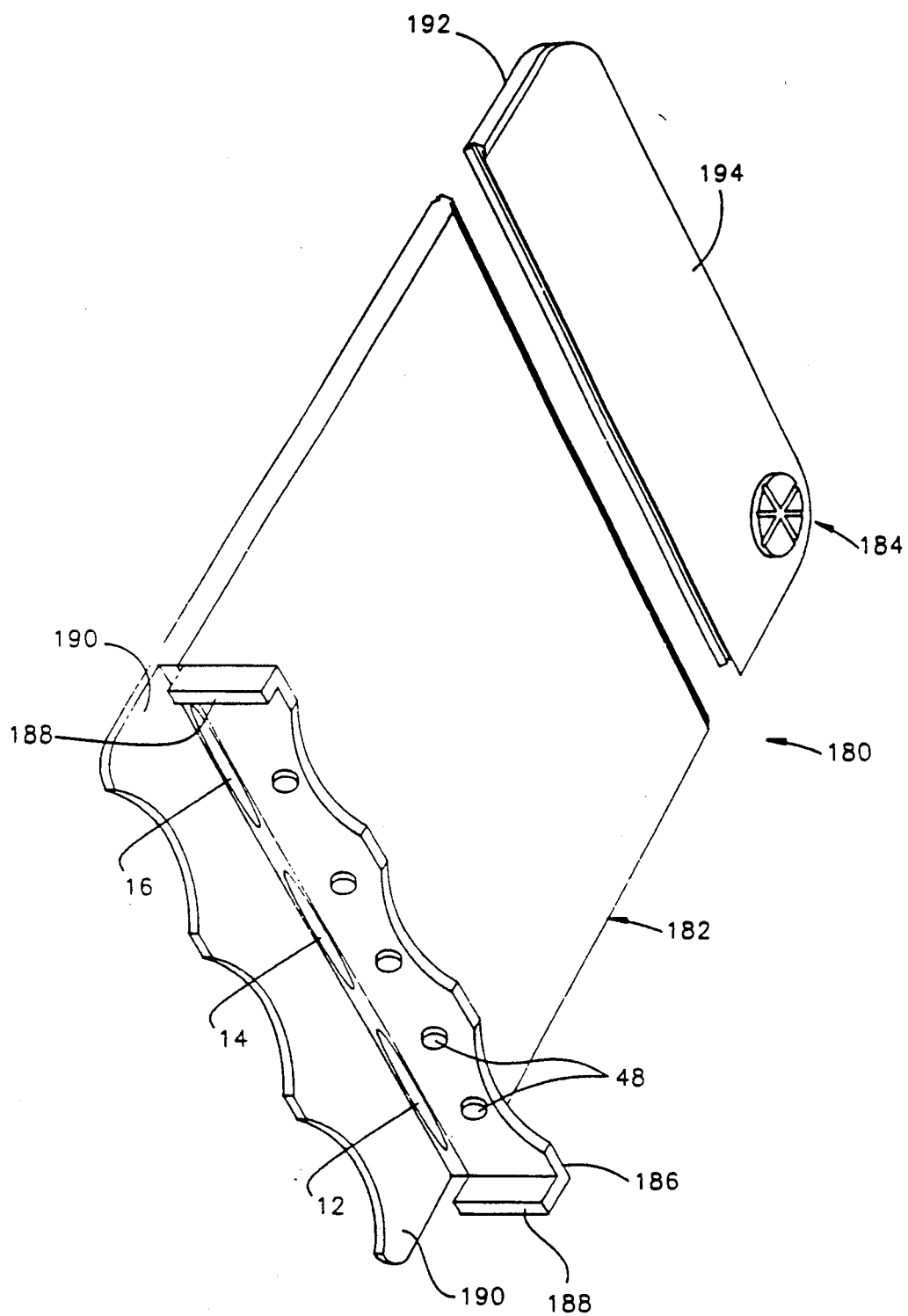
FIG. 12 shows an alternative embodiment of the body of the syringe of FIG. 1 having a replaceable, interchangeable dispenser section.

Syringe 2 also includes a stem 32 sized to fit substantially fully within cutout 14 when accumulator piston 30 is adjacent body supports 33 as shown in FIG. 3. Stem 32 has raised finger grips 34 at its proximal end 36, proximal end 36 being enlarged to provide a good surface for the user to press against. The proximal edge 38 of body 4 has a scalloped shape to accommodate the arcuate shape of proximal end 36 to permit a generally flush appearance as suggested in FIG. 3. Stem 32 also has a longitudinal guide slot 42 and a transverse guide slot 44, guide slot 44 being positioned near the distal end 46 of stem 32. Slots 42, 44 are made to receive cylindrical guide pegs 48 which extend from the underside of that portion of base 6 overlying cutouts 10, 12, 14 along proximal edge 38. Guide pegs 48 are best illustrated in FIG. 12 but are also shown in dashed lines FIG. 1; their positions are suggested in FIG. 3 by broken circles. The guide pegs 48 that are aligned with cutouts 10-14 travel along guide slot 42 as stem 32 moves along cutouts 10-14. Transverse guide slot 44 is used, as discussed below, after stem 32 has been substantially removed from body 4 and moved laterally to another cutout. The use of guide pegs 48 and guide slots 42, 44 both keeps stem 32 properly aligned within the cutouts during use and also prevents stem 32 from being completely removed from body 4 to both prevent its loss and to maintain distal end 46 within accumulator chamber 31 for enhanced sanitation.

The inner surfaces of elliptical cutouts 10, 12, 14 may be coated with a pharmaceutically compatible, low friction material, such as PTFE sold by the DuPont Corporation of Wilmington, Del. under the trademark TEFLON. Other coatings, which are ideally hard, low friction and inert, can be used as well. For example, a thin coating may be deposited onto the surfaces of cutouts 10, 12, 14 by appropriate vapor deposition processes.

Referring now primarily to FIGS. 1, 2A-14 2C, and 4, valve body 28 is made of an elastomeric material, preferably a silicon elastomer such as that made by Dow Chemical Company of Midland, Mich. as Q7-4765. Valve body 28 is illustrated in these figures as it would exist when stem 32 is pressing first piston 20 thus forcing first liquid 52 within the first reservoir 24 through a first flow path 54, formed in base 6, through vale body 28 and into accumulator chamber 31. To do so, valve body 28 includes first and second blind flow paths 56, 58. Blind flow paths 56, 58 are preferably circular blind holes formed in valve body 28. Valve body 28 also includes first and second normally closed slits 60, 62 formed in valve body 28 after valve body has been formed. Slits 60, 62, which are in the preferred embodiment 0.100" wide, can be made by forcing a thin blade, 0.006" thick and 0.100" wide, into the face 64 of valve body 28 at positions chosen to intersect flow paths 56, 58.

The thickness of valve body 28 at edges 66, 68 is about 0.062" and is preferably slightly greater than the depth of cutout 27; the width of face 64 is preferably equal to or slightly longer than the width of cutout 27. Thus, when cover 8 is mounted to base 6, valve body 28 acts to seal accumulator chamber 31 from first and second reservoirs 24, 26 except for the flow paths formed by blind flow paths 56, 58 and slits 60, 62.

Figure 4:
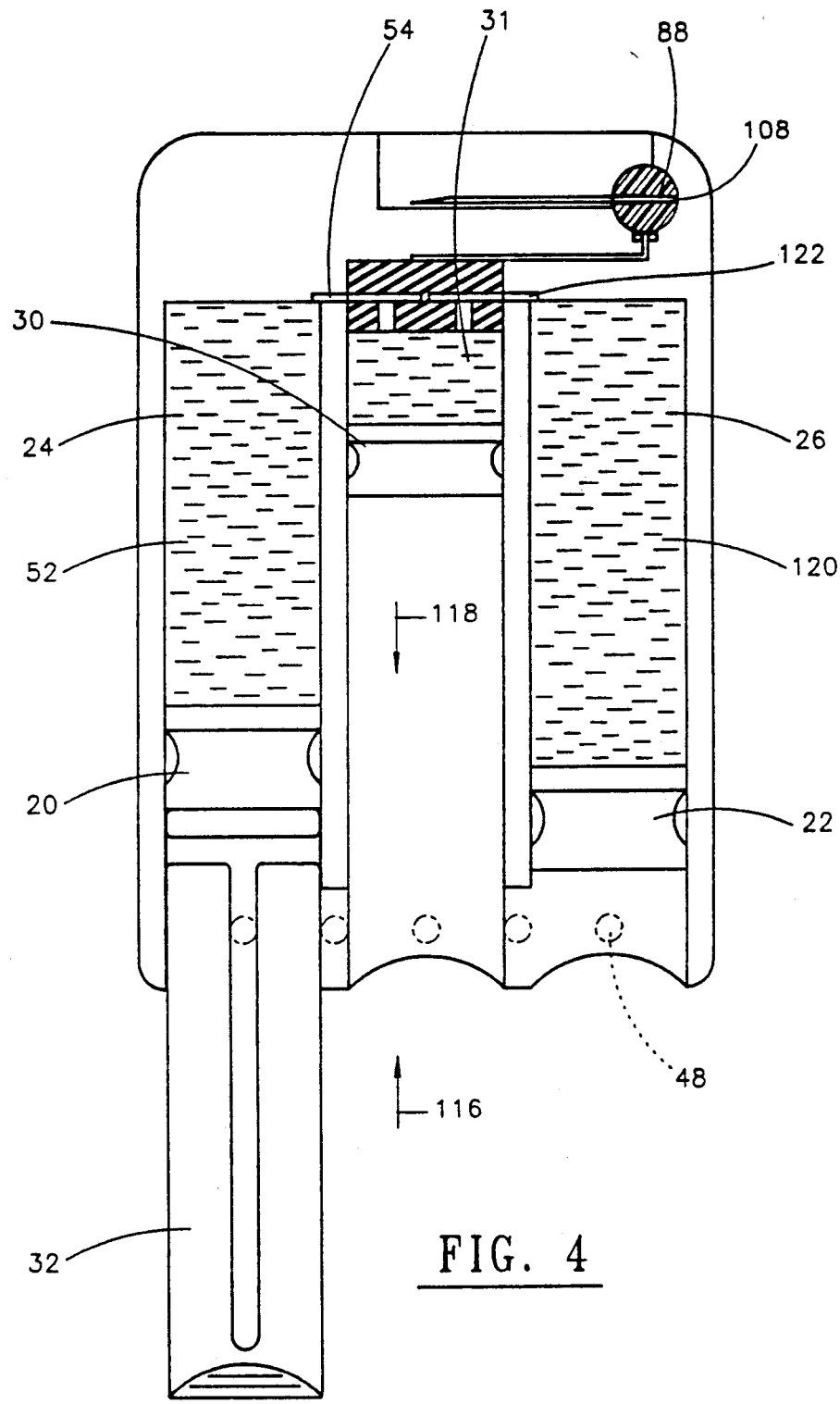
FIG. 4 shows the syringe of FIG. 3 with the first liquid pharmaceutical in the first reservoir being forced into the accumulator chamber, thus moving the accumulator piston from the position of FIG. 3 to the position of FIG. 4.

Valve block 28 also includes a cutout region 70 spaced apart from edges 66, 68. Cutout region 70 is about 0.010" deep and permits the opening of slits 60, 62 when first and second reservoirs 24, 26 are pressurized by the use of stem 32. FIGS. 2, 2B and 2C illustrate, in a somewhat exaggerated form, the opening of first slit 60 due to pressurization of liquid 52 within first variable volume reservoir 24 by stem 32 as illustrated in FIG. 4. As seen in FIGS. 2B and 2C, surface 72 created by cutout region 70 lying above first slit 60 is permitted to bow upwardly thus permitting first slit 62 to open thus opening a fluid path between first reservoir 24 and accumulator chamber 32. However, second slit 62 acts as a check valve, partially due to the pressurized fluid within accumulator chamber 31 pressing on its overlying surface 74, to prevent flow from accumulator chamber 31 to second reservoir 26 during this operation.

Syringe 2 further includes a rotatable needle assembly 78 mounted to body 4. Needle assembly 78 includes a hub assembly having a hub 82 and end flanges 84, 86. Hub 82 has a bore 88 formed therethrough for receipt of one end 90 of a hollow needle 92. Needle 92 is secured within base 88 by an epoxy adhesive 93. Cover 8 and base 6 include holes 94, 96 sized for receipt of hub 82. The axial length of hub 82 is about equal to the combined thickness of base 6 and cover 8. With end flange 84 resting against the outer surface 102 of cover 8 and end flange 86 resting against the outer surface 98 of base 6, flange 86 is secured to hub 82, such as with an adhesive, to securely mount needle assembly 78 to body 4.

Figure 5:
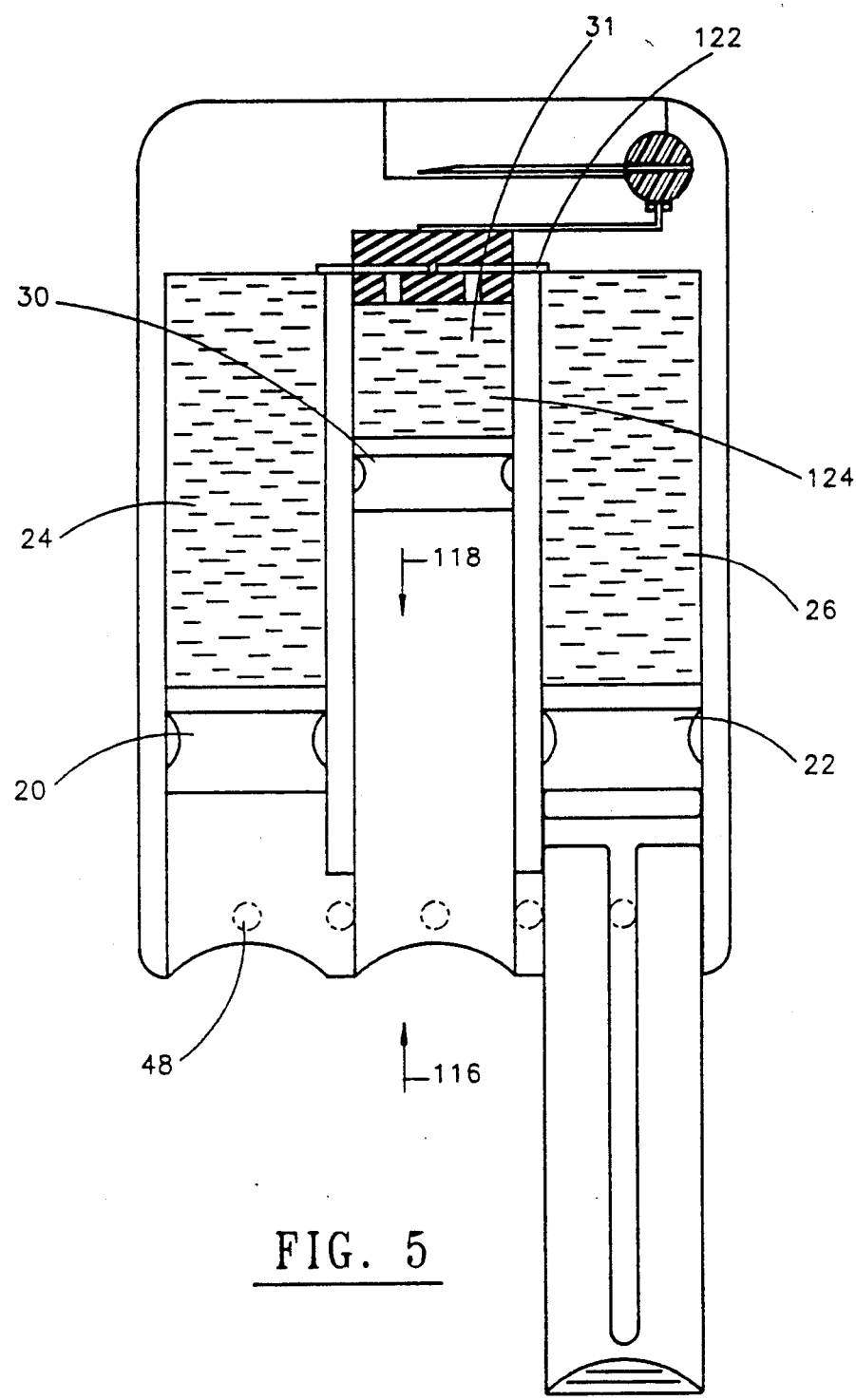
FIG. 5 illustrates displacing the liquid pharmaceutical from the second reservoir into the accumulator chamber where it mixes with the first liquid pharmaceutical.
Figure 6:
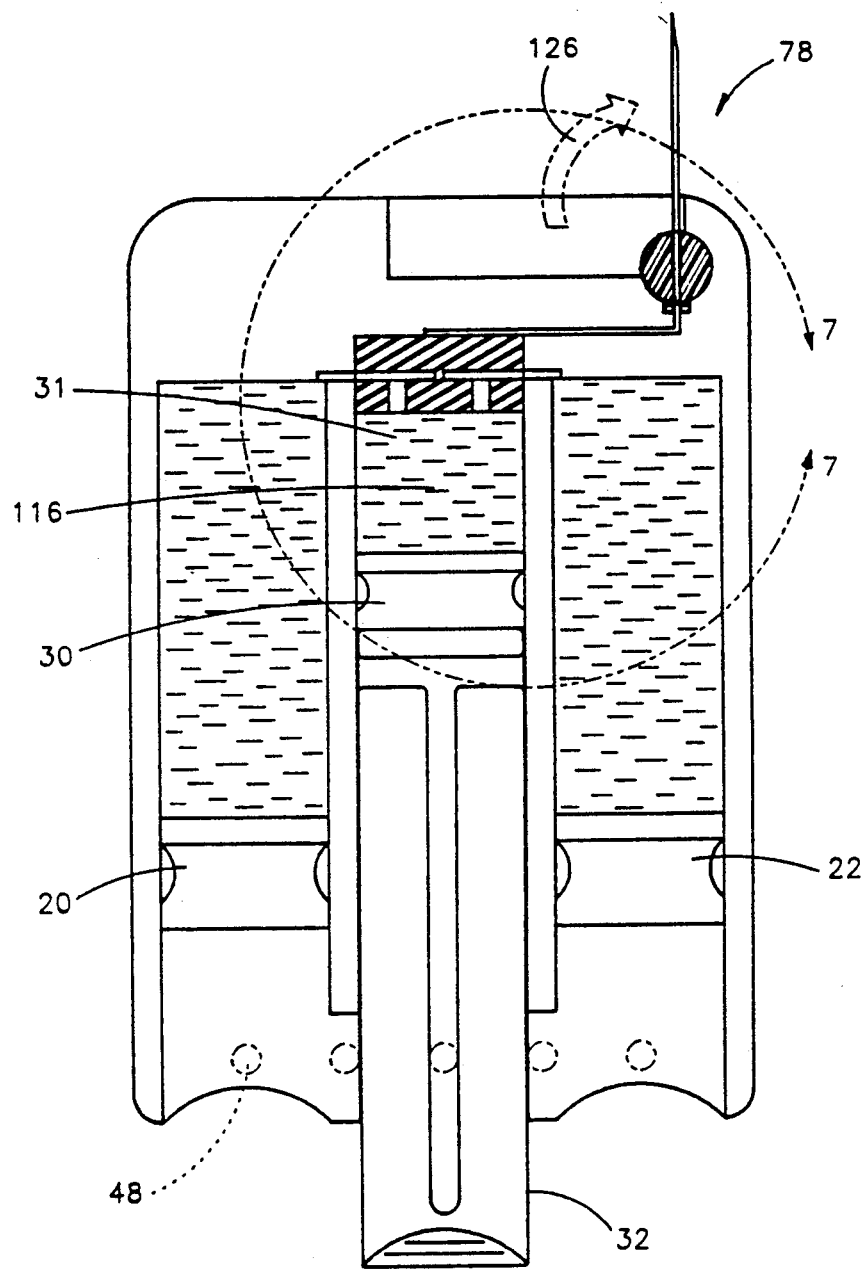
FIG. 6 shows the syringe of FIG. 5 with the needle assembly moved from its stored position of FIG. 5 to its extended position of FIG. 6 and the expulsion of the now mixed pharmaceutical liquid from the accumulator chamber, through the exit path and through the hollow needle.

The pivotal movement of needle assembly 78 between the stored or retracted position of FIGS. 3-5 and the extended position of FIG. 6 is limited by the engagement of a cylindrical peg 105, extending from end flange 84, which rides within a slot 100 formed in outer surface of 102 of cover 8. As suggested in FIG. 2, slot 100 narrows somewhat near its ends to provide a detenting action with peg 94 to help keep needle assembly 78 from inadvertently pivoting when in its retracted or extended positions. Base 6 has a cutout 104 intersecting hole 96 to provide a safe place for receipt of needle 92 when syringe 2 is not in use. A removable protective sheath may be used with needle assembly 78, if desired.

Figure 7:
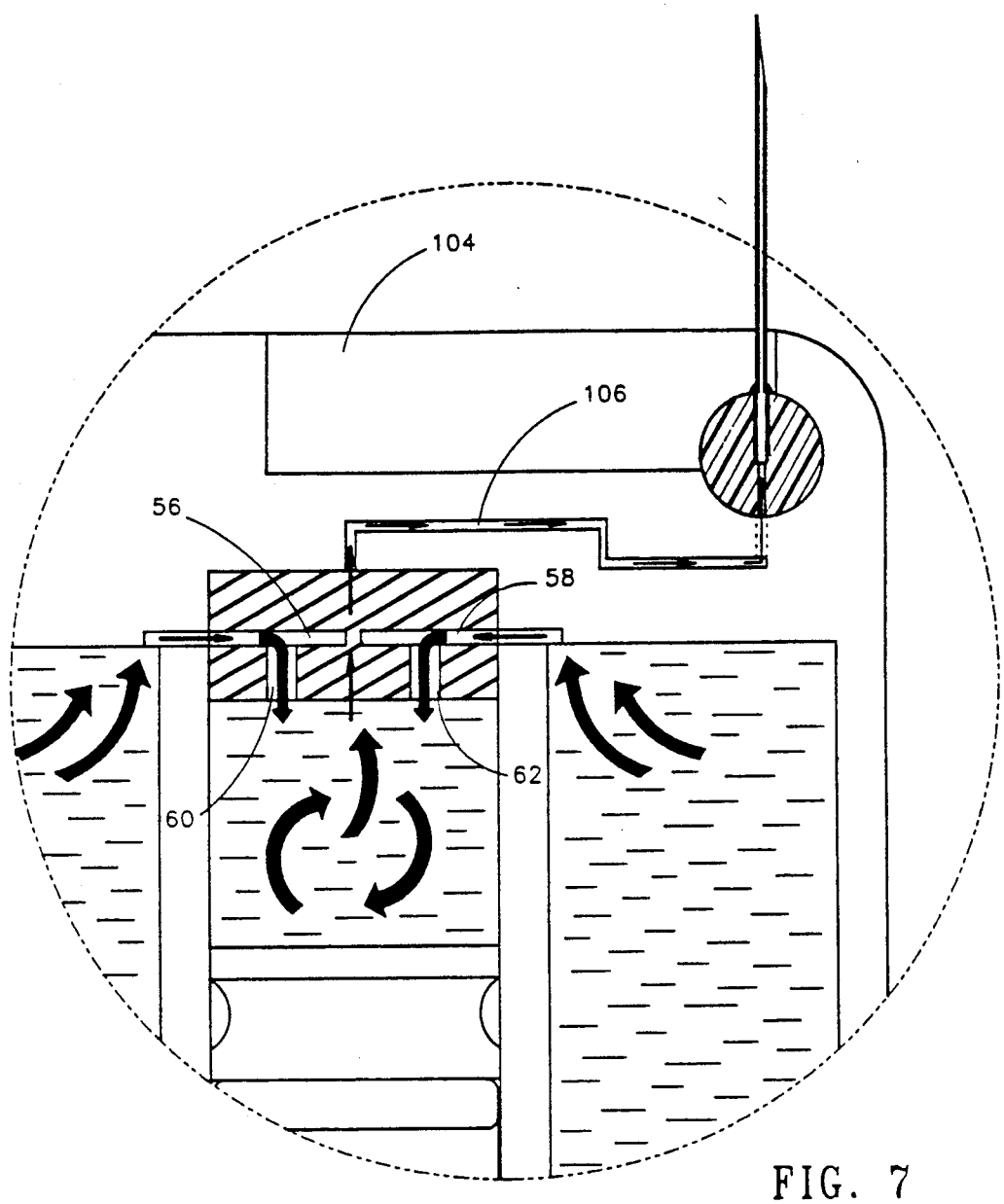
FIGS. 7 and 7a are enlarged views illustrating the simultaneous flow of liquid from both the first and second reservoirs, through the valve block, and into the accumulator chamber, and then from the accumulator chamber, through the exit path, and out the hollow needle.
Figure 7A:
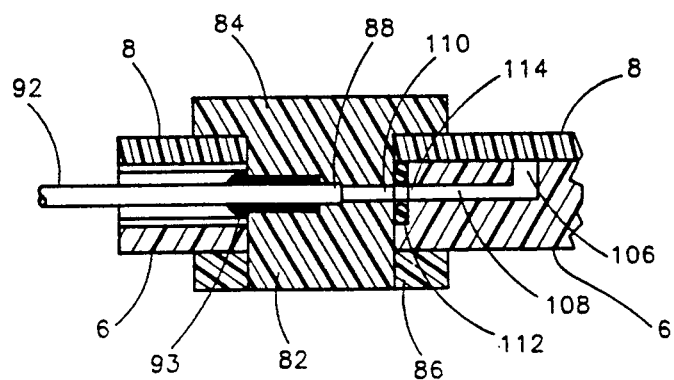

An exit path 106 is formed in base 6 and intersects elongate cutout 14 at a position adjacent cutout region 70 of valve body 28. Path 106 fluidly couples accumulator chamber 31 with an end 110 of bore 88 when needle assembly 78 is in the extended position of FIGS. 6 and 7. Exit path 106 is created by an open top groove formed in base 6 for most of its length. However, a portion 108, shown in FIG. 7A, is formed in base 6 and opens into hole 96 to connect end 110 of bore 88 to exit path 106. An O-ring 112 is positioned at the terminal end 114 of portion 108 of exit path 106 to create a seal against hub 82. Other types of seals can be used as well.

Figures 10A, 10B:
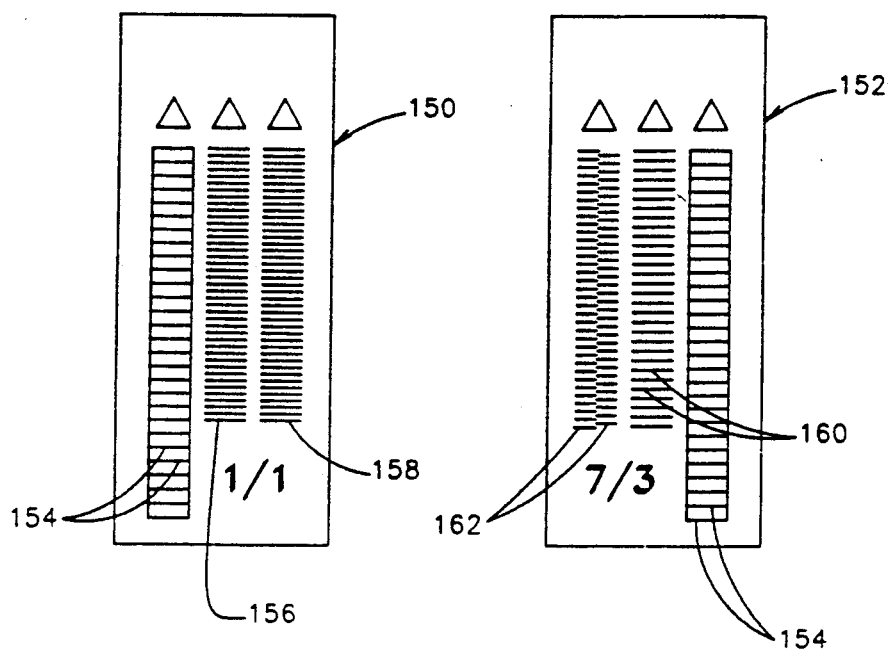
FIGS. 10A and 10B are front views of transparent dosage labels.

The amount of liquids 52, 120 forced into accumulator chamber 31 can be gauged through the use of transparent dosage labels 150, 152 shown in FIGS. 10A and 10B. Label 150 includes accumulator calibrations 154. Labels 150, 152 are transparent except for the marking shown in FIGS. 10A and 10B to provide an unimpeded view of the contents of reservoirs 24, 26 and accumulator chamber 31. The space between each calibration 154 equals one unit of medication. Label 150 also include first and second pharmaceutical calibrations 156, 158. Calibrations 156, 158 are each spaced apart by distances equal to one-half of a unit of medicine. Therefore, if the user moves pistons 20, 22 from one calibration 156, 158 to the next calibration 156, 158, equal amounts (one-half unit each) of liquids 52, 120 will be forced into accumulator chamber 31 to move piston 30 a distance equal to the distance between successive calibrations 154.

Label 152, mounted to the opposite side of body 4 as label 150, is used when the proportion of first liquid 52 to second liquid 120 is 7 to 3. The distance between successive first and second pharmaceutical calibrations 160, 162 corresponds to 70% of a unit and 30% of a unit respectively. Note that successive calibrations 162 are staggered—otherwise they could be too close together for easy reading. Labels 150, 152 are preferably removable so that labels having other calibrations for other proportions and dosages can be used as well.

In use, syringe 2 is preferably obtained in the initial, as-shipped condition of FIG. 3. Stem 32 is withdrawn from cutout 14, moved to the left to into alignment with elongate cutout 10 and pushed in the direction of arrow 116. Doing so forces liquid 52 into variable volume accumulator chamber 31 and causes accumulator piston 30 to move in the direction of arrow 118. After a sufficient amount of liquid 52 has been forced into accumulator chamber 31 from first reservoir 24, stem 32 is moved in the direction opposite arrow 116 and then moved laterally until it is aligned with elongate cutout 12. Stem 32 is then driven in the direction of arrow 116 forcing second liquid 20 within second variable volume region 26 along a second flow path 122, through valve body 28 and into accumulator chamber 31 to create a mixed liquid 124 as shown in FIG. 5.

Figure 8:
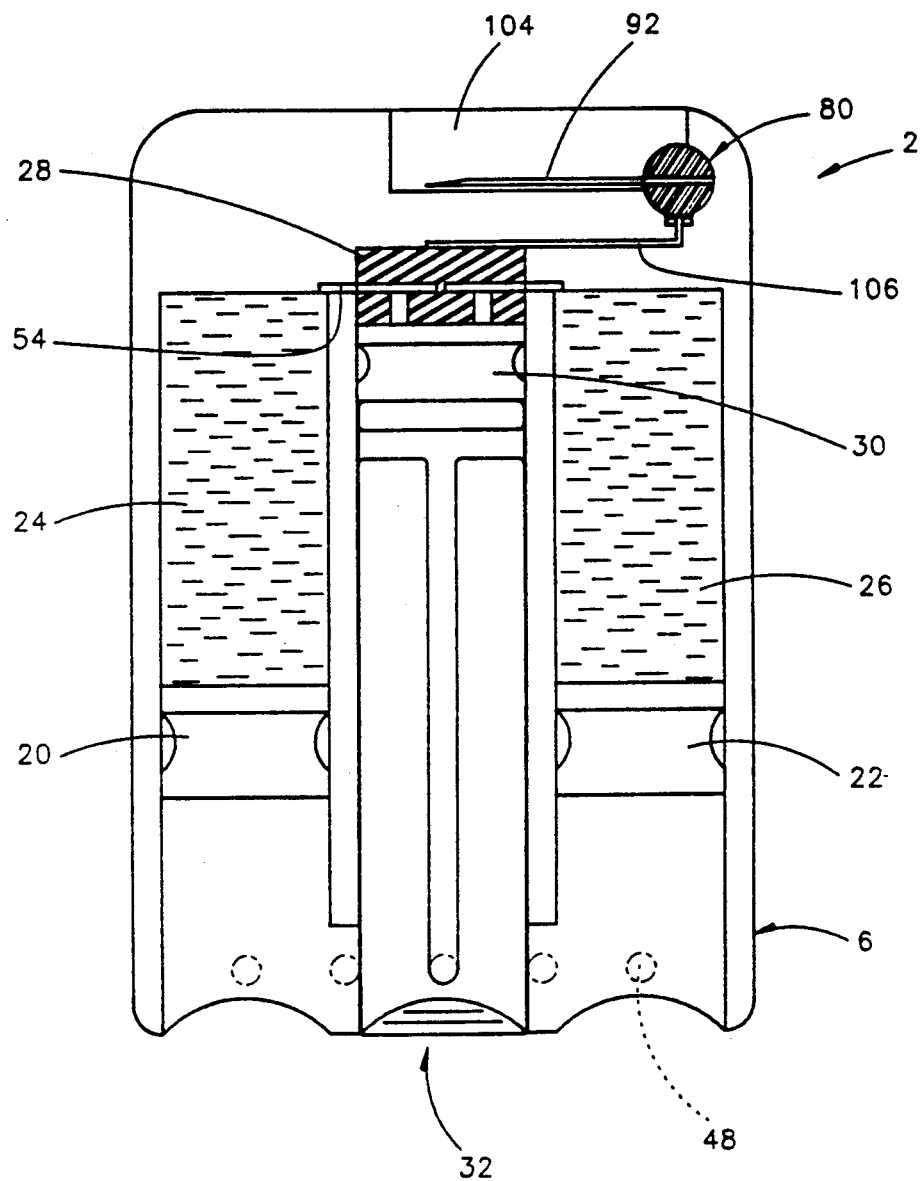
FIG. 8 shows the syringe of FIG. 6 in its post-use, storage condition.

Next, needle assembly 78 is moved in the direction of arrow 126 to the extended position of FIG. 6. This is preferably accomplished by grasping the outer grooved surfaces 128 formed in hub assembly 80. Stem 32 is used to drive accumulator piston 30 in the direction of arrow 116 to force mixed liquid 124 past cutout region 70, through exit path 106, through bore 88 and through hollow needle 92. At the end of the injection, stem 32 is in the position of FIG. 8 and needle assembly 78 is rotated back to its stowed position as shown in FIG. 8.

Figure 9:
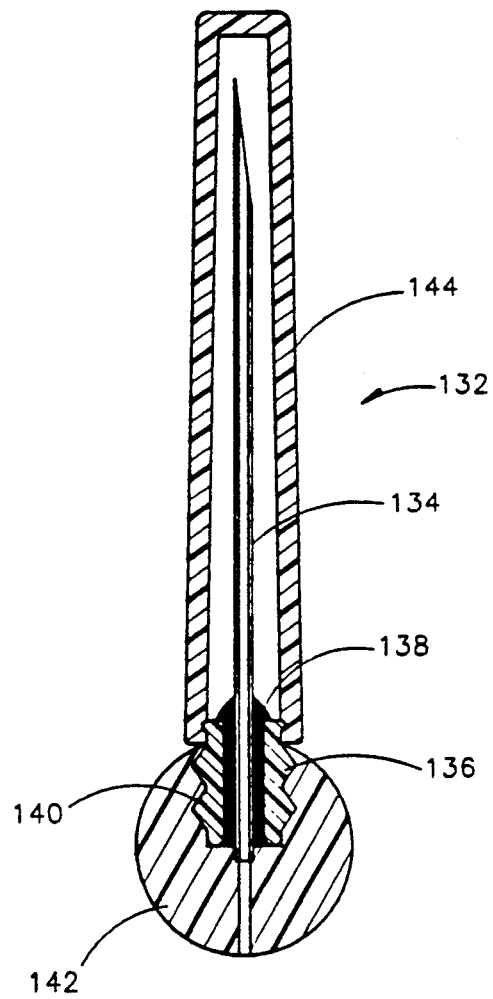
FIG. 9 is an enlarged cross-sectional view of an alternative needle assembly of FIG. 1 including a removable needle covered by a protective sheath.

FIG. 9 illustrates an alternative embodiment of needle assembly 78. Needle assembly 132 includes a needle 134 mounted to a threaded adapter 136 by an epoxy adhesive 138. Adapter 136 mounts to a threaded hole 140 formed in hub 142 to permit needle 134 to be easily and quickly replaced when needed. Assembly 132 also includes a safety sheath 144 which snaps onto an end of adapter 136 to help prevent inadvertent needle sticks and to help keep needle 134 clean.

Figures 11A, 11B:
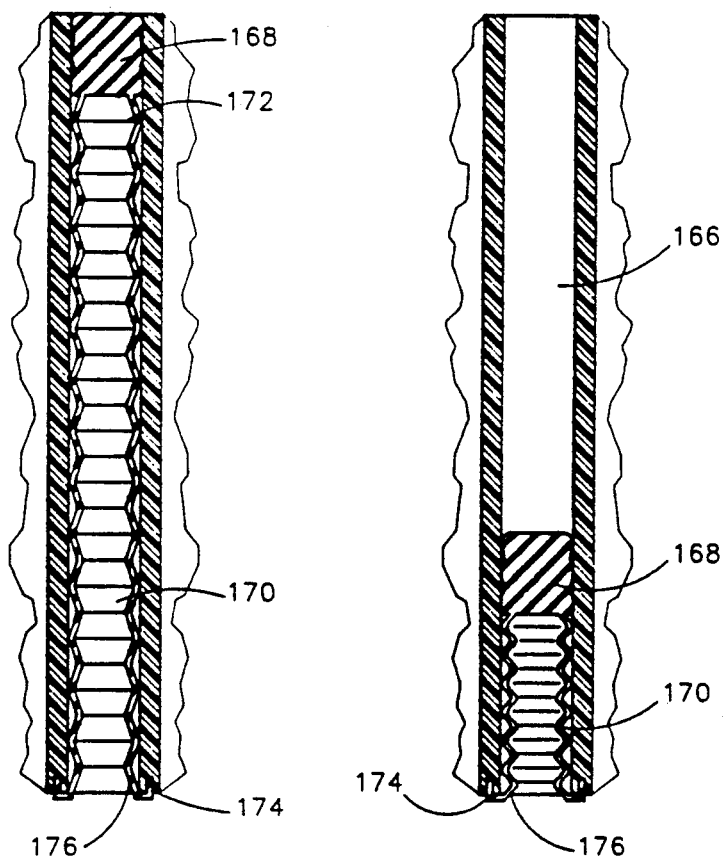
FIGS. 11A and 11B are simplified views showing the accumulator piston and chamber of FIGS. 3 and 4 used with a sterility skirt.

FIGS. 11A and 11B illustrate, in simplified form, an accumulator chamber 166 housing an accumulator piston 168 and a sterility skirt 170. Skirt 170 is a lightweight, fluid impervious, flexible tubular material, such as silicone rubber, secured to piston 168 at one end 172 of skirt 170 and to the proximal end 174 of chamber 166 at the other end 176 of skirt 170. Skirt 170 is in its extended condition of FIG. 11A when piston 168 is fully within chamber 166 and is in its compressed condition of FIG. 11B when piston 168 is near proximal end 174. Therefore, skirt 170 and piston 168 help to keep the inner walls of chamber 166 sterile during use and between uses. Other methods for insuring sterility is maintained can be used as well.

FIG. 12 illustrates an alternative embodiment of syringe body 4. Syringe body 180 includes a base 182 and a dispenser section 184. Base 182 includes a hinged end 186 shown in an open configuration prior to mounting stem 32 into cutout 12. Hinged end 186 is pivoted downwardly until surfaces 188, 190 meet and are secured together, such as through ultrasonic welding techniques, to secure stem 32 within body 180.

Dispenser section 184 includes a base portion 192 and a cover portion 194. Dispenser section 184 can include the structure shown with respect to the embodiment of FIGS. 1-8. Other dispenser sections can be made to be interchangeable with the same base 182 to permit flowable pharmaceuticals to be dispensed in different ways.

Figure 13:
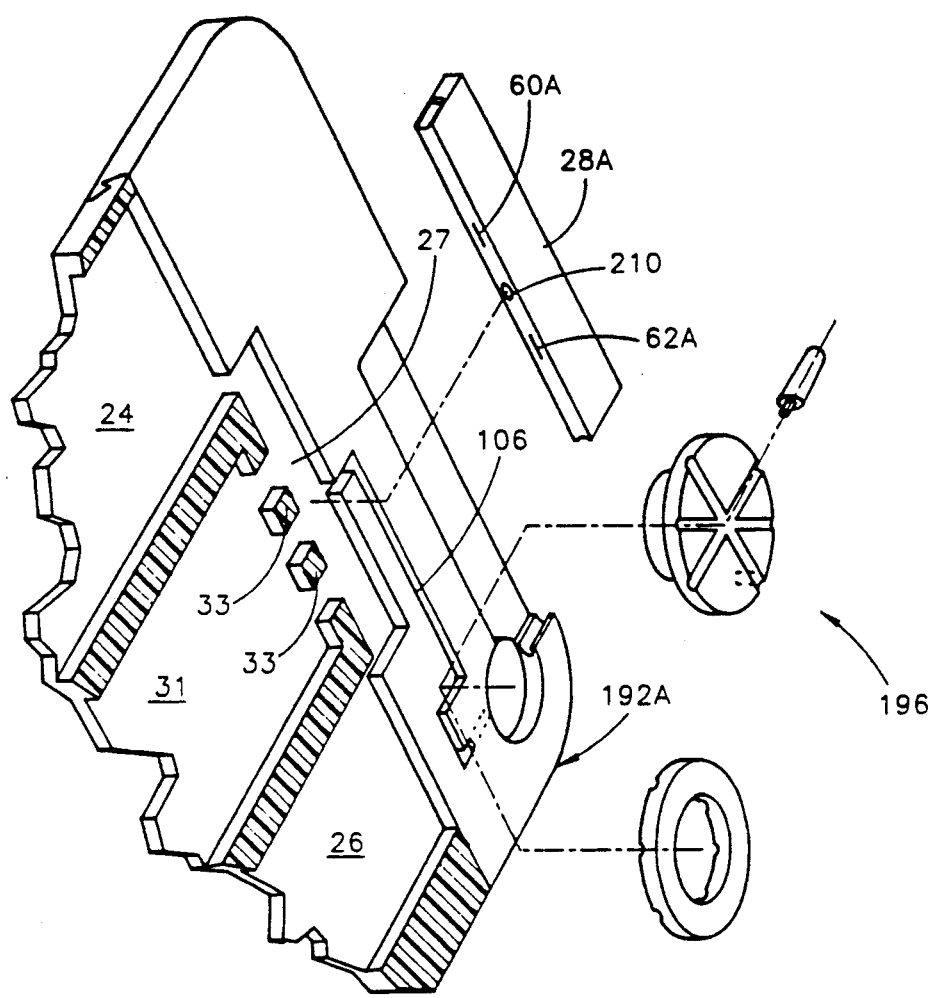
FIG. 13 shows the base portion of the dispenser section of FIG. 12 used with a spray nozzle as the delivery head.

FIG. 13 illustrates a base portion 192A configured for use with a dispenser section of the type including a spray nozzle assembly 196 instead of needle assembly 78. Valve block 28A is modified to eliminate cutout 70; instead of cutout 70, a similarly positioned cutout (not shown) is formed in the inner surface of the overlying cover portion 194 to permit slits 60A, 62A to open when subjected to pressure from reservoirs 24, 26. A cutout 70, or its equivalent formed in cover portion 194, is not needed if the pressure needed to open slits 60, 62 is sufficiently greater than the pressure required to push actuator piston 30 along cutout 14 so that piston 30 will move along cutout 14, thus enlarging actuator chamber 31, before opening the other, non-pressurized slit 62, 60. Also, valve block 28A includes a bore 210 to provide a fluid flow path between accumulator chamber 31 and exit bore 106. Otherwise the structure of base portion 192A is similar to the corresponding structure of syringe 2 shown in FIG. 2.

Figure 14:
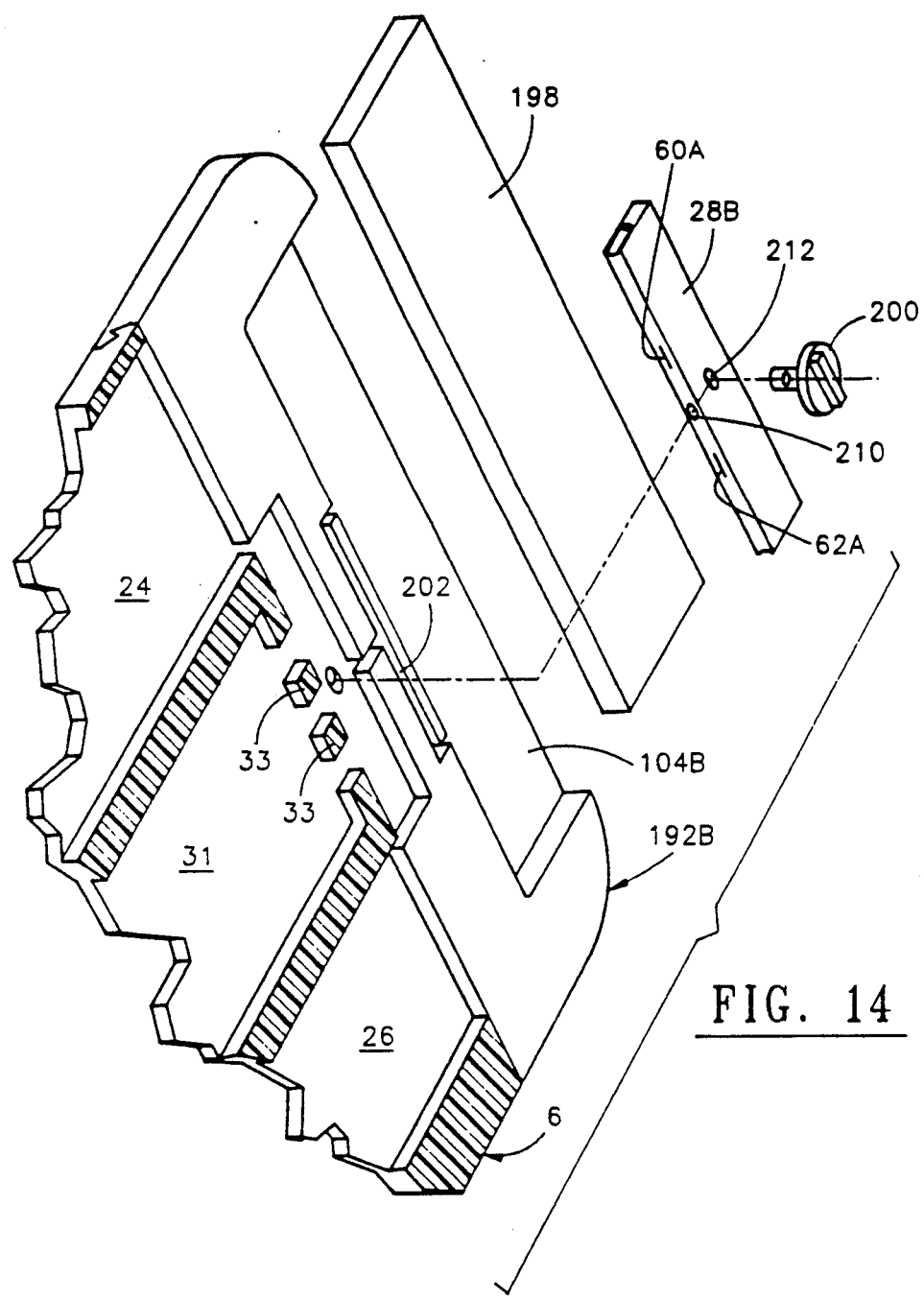
FIG. 14 illustrates an alternative embodiment of the dispenser section of FIG. 13 with the spray nozzle replaced by a sponge pad-type topical pharmaceutical applicator.

FIG. 14 illustrates a base portion 192B having a pharmaceutical dispensing sponge pad 198 mounted within a cutout 104B. The flow of mixed pharmaceutical is controlled by a valve 200 mounted to the dispenser section and through a bore 212 formed in valve body 28B. Bore 212 intersects bore 210 so valve 200 controls fluid flow from accumulator chamber 31, through bore 210, along an exit path 202 and to sponge pad 198. This embodiment permits the user to mix two pharmaceuticals within chamber 31 and then deliver the mixed pharmaceuticals to sponge pad 198 for topical application, typically directly to a patient or indirectly through a bandage, pad or patch.

Figure 15:
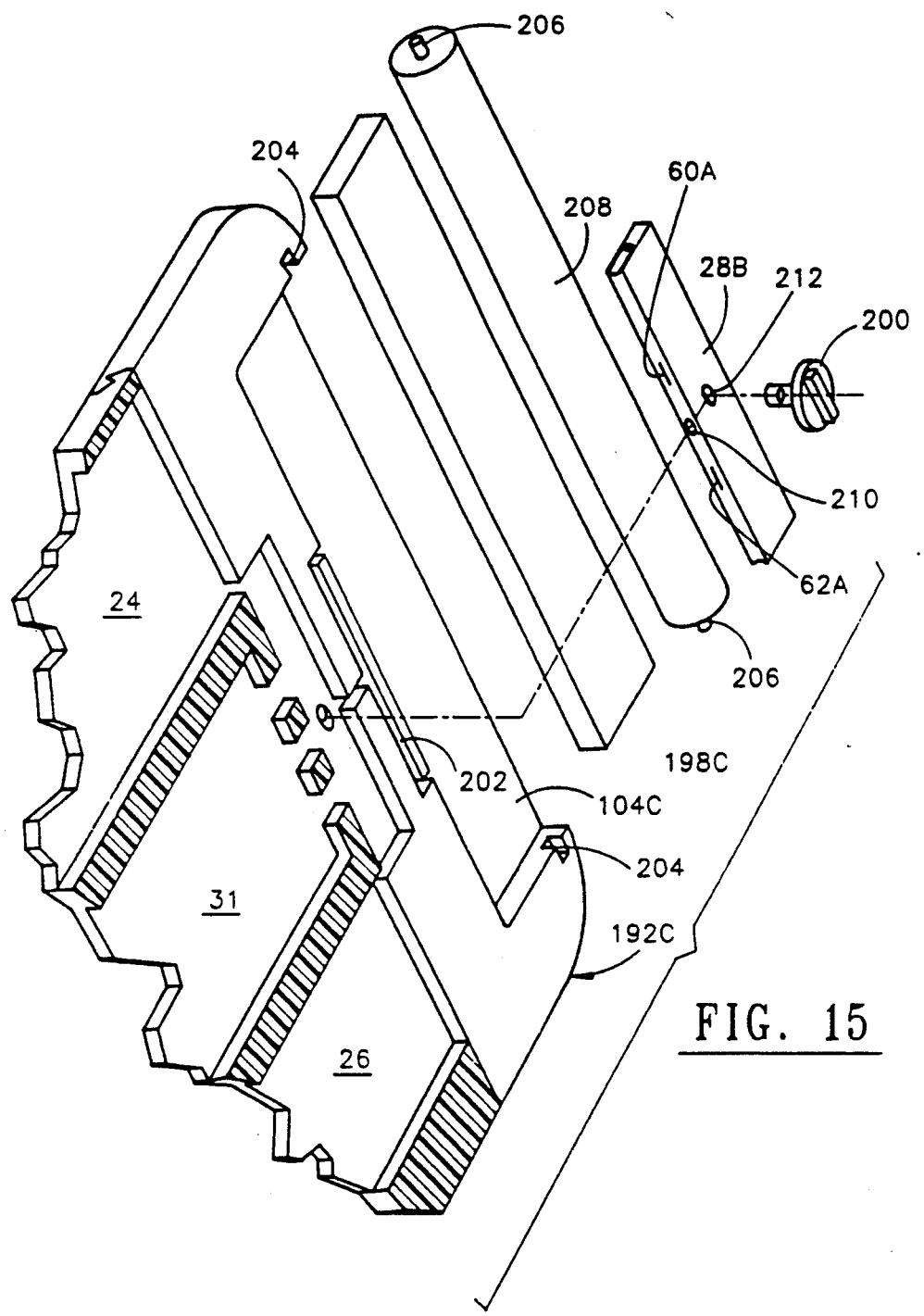
FIG. 15 illustrates an alternative embodiment of the base portion of FIG. 13 in which the spray nozzle has been replaced by a roller-type topical pharmaceutical applicator.

FIG. 15 illustrates a further base portion 192C which is similar to base portion 192B with the exception that a pair of cutouts 204 are formed therein to accommodate the tips 206 of an application roller 208. Sponge pad 198C is smaller than sponge pad 198 to leave room within cutout 104C for roller 208. This dispensing section embodiment is also used for the topical application of a mixed pharmaceutical.

Other modifications and variation can be made to the disclosed embodiments without departing from the subject of the invention as defined in the following claims. For example, instead of using check valve structures to the prevent the reverse flow of fluid back into reservoirs 24, 26, pistons 20, 22 could be made so that they are one way pistons, that is so that they move only in the direction of arrow 116. More than two reservoirs may be used; an additional reservoir could be used to house a sterile saline solution used to flush out the syringe between uses. Also, the physical arrangement of the reservoirs relative to the accumulator chamber can be changed. Instead of having the reservoirs be integrally made with body 4, they could be separately constructed containers, such as conventional syringe cartridges of the type having a septum at one end, an exposed piston at the other and filled with a liquid pharmaceutical. Valve block 28 could be constructed with slits 60, 62 passing completely through the valve block; this would permit the slits to open directly into reconfigured flow paths 54, 122 so to eliminate the need for blind flow paths 56, 58. The needle assembly could be in a fixed orientation relative to the body or slidably mounted to the body. Different types of valves and flow paths could be used to selectively fluidly couple needle 92 to accumulator chamber 31. The invention generally has been described with respect to liquid pharmaceuticals; the invention is intended to cover both readily flowable liquids and flowable, but more viscous, creams and salves as well.

What is claimed is:

1. A variable ratio, liquid pharmaceutical dispensing system comprising:

first and second variable volume liquid reservoirs containing first and second liquids;

a variable volume accumulator chamber;

means for permitting fluid flow from the first and second reservoirs into the variable volume accumulator chamber while preventing backflow;

a pharmaceutical delivery head;

means, including a manually movable element movable by a user between open and closed positions, for permitting and blocking fluid flow from the variable volume accumulator chamber to the pharmaceutical delivery head when the movable element is in the open and closed positions respectively;

means for forcing first and second volumes of the first and second liquids from the first and second reservoirs, respectively, to the variable volume accumulator chamber via the fluid flow permitting means when the movable element is in the closed position, so that the volume of the variable volume accumulator chamber increases by an amount equal to the first and second volumes combined, and the first and second volumes of the first and second liquids creates a liquid mixture in the variable volume accumulator chamber; and means for expulsing the liquid mixture from the variable volume accumulator chamber through the pharmaceutical delivery head via the fluidly coupling means.

2. The system of claim 1 wherein the first and second variable volume reservoirs are elongate with generally constant cross-sectional shapes.

3. The system of claim 2 wherein the first and second variable volume reservoirs each has an elliptical cross-sectional shape.

4. The system of claim 2 wherein the first and second variable volume reservoirs are partially defined by first and second pistons.

5. The system of claim 1 wherein the first and second reservoirs and the variable volume accumulator chamber are defined by a common body.

6. The system of claim 5 further comprising calibration markings on the common body.

7. The system of claim 1 wherein the pharmaceutical delivery head includes a hollow hypodermic needle having a tip.

8. The system of claim 7 wherein:

the common body has a needle storage region sized to house the needle therein; and the hollow needle is movably mounted to the common body for movement between a storage position, with the needle within the needle storage region, and a use position, with the tip of the needle external of the needle storage region.

9. The system of claim 8 wherein the hollow needle is pivotally mounted to the common body.

10. The system of claim 1 wherein the permitting means includes first and second check valves operably positioned between the first and second reservoirs and the variable volume accumulator chamber.

11. The system of claim 1 wherein the flowable material delivery head includes a spray nozzle assembly.

12. The delivery system of claim 1 wherein the flowable material delivery head includes a topical applicator.

13. The delivery system of claim 12 wherein the topical applicator includes a roller applicator.

14. The system of claim 1 further comprising means for keeping the accumulator chamber sterile.

15. A variable ratio multipharmaceutical delivery system comprising:

first and second variable volume reservoirs containing first and second flowable materials;

a variable volume accumulator chamber;

means for permitting fluid flow from the first and second reservoirs into the variable volume accumulator chamber while preventing backflow;

a flowable material delivery head;

means for fluidly coupling the delivery head to the variable volume accumulator chamber;

means for forcing first and second volumes of the first and second flowable materials from the first and second reservoirs, respectively, to the variable volume accumulator chamber via the fluid flow permitting means, so that the volume of the variable volume accumulator chamber increases by an amount equal to the first and second volumes combined, the first and second volumes of flowable materials forced into the variable volume accumulator chamber creates a flowable material mixture therein; and the permitting means including an elastomeric valve body having first and second normally closed slits, said slits having reservoir ends fluidly coupled to the first and second reservoirs respectively, and each of said slits having accumulator ends fluidly coupled to the variable volume accumulator chamber;

means for maintaining the second slit closed when the reservoir end of the first slit is subjected to a fluid pressure sufficient to open the first slit to permit the pressurized flowable material to pass through the opened slit and into the variable volume accumulator chamber; and means for expulsing the flowable material mixture from the variable volume accumulator chamber through the delivery head via the fluidly coupling means.

16. The system of claim 15 wherein the maintaining means includes first and second deflectable surfaces formed on the valve body and aligned with the first and second slits so that applying a pressurized flowable material to one of the reservoir ends causes the corresponding first or second deflectable region to deflect.

17. The system of claim 16 wherein the first and second deflectable surfaces are in fluid communication with the variable volume accumulator chamber so that the presence of pressurized flowable material in the variable volume accumulator chamber tends to seal the other of the first and second slits.

18. The system of claim 17 wherein the delivery head coupling means includes a fluid path segment across the first and second deflectable surfaces.

19. A syringe comprising:

first and second liquid reservoirs containing first and second liquids, each of said reservoirs having a length and first and second ends and a generally constant cross-sectional shape along at least a part of the length;

first and second pistons mounted within the first and second reservoirs and movable towards the first ends thereof;

an accumulator chamber having a length and first and second ends, at least part of the length of the accumulator chamber having a generally constant cross-sectional shape;

an accumulator piston mounted within the accumulator chamber and movable along the length of the accumulator chamber;

a flow path fluidly coupling the first ends of the first and second reservoirs to the accumulator chamber;

a stem for selectively driving the first piston, the second piston and the accumulator piston towards the respective first ends of the first reservoir, the second reservoir and the accumulator chamber;

means for preventing fluid flow from the accumulator chamber into either of the first and second reservoirs so that when the first piston is driven towards the first end of the first reservoir by the stem, liquid in the first reservoir flows into the accumulator chamber so to tend to force the accumulator piston towards the second end of the accumulator chamber;

a hollow needle; and means for selectively fluidly coupling the accumulator chamber to the hollow needle so that when fluidly connected, any liquid in the accumulator chamber can be forced through the fluidly coupling means and to the hollow needle by driving the accumulator piston towards the first end of the accumulator chamber by the stem.

20. A variable ratio, liquid pharmaceutical dispensing system comprising:

first and second pistons;

an accumulator piston;

first and second variable volume reservoirs containing first and second liquids, wherein the first and second variable volume reservoirs are elongate with generally constant cross-sectional shapes, and the first and second variable volume reservoirs are partially defined by the first and second pistons;

a variable volume accumulator chamber, wherein the variable volume accumulator chamber is partially defined by the accumulator piston housed within the variable volume accumulator chamber;

means for permitting fluid flow from the first and second reservoirs into the variable volume accumulator chamber while preventing backflow;

a pharmaceutical delivery head;

means, including a manually movable element movable by a user between open and closed positions, for permitting and blocking fluid flow from the variable volume accumulator chamber to the pharmaceutical delivery head when the movable element is in the open and closed positions respectively;

means for forcing first and second volumes of the first and second liquids from the first and second reservoirs, respectively, to the variable volume accumulator chamber via the fluid flow permitting means, so that the volume of the variable volume accumulator chamber increases by an amount equal to the first and second volumes combined, and the first and second volumes of the first and second liquids creates a liquid mixture in the variable volume accumulator chamber; and means for expulsing the liquid mixture from the variable volume accumulator chamber through the pharmaceutical delivery head via the fluidly coupling means, the expulsing means including the accumulator piston.

21. The system of claim 20 further comprising a collapsible sterility skirt connected to the accumulator piston and to the variable volume accumulator chamber to aid keeping the variable volume accumulator chamber sterile.

22. A pharmaceutical delivery system comprising:

first and second liquid reservoirs containing first and second liquids, each of said reservoirs having a length and first and second ends and a generally constant cross-sectional shape along at least a part of the length;

first and second pistons mounted within the first and second reservoirs and movable towards the first ends thereof;

an accumulator chamber having a length and first and second ends, at least part of the length of the accumulator chamber having a generally constant cross-sectional shape;

an accumulator piston mounted within the accumulator chamber and movable along the length of the accumulator chamber;

a flow path fluidly coupling the first ends of the first and second reservoirs to the accumulator chamber;

a stem for selectively driving the first piston, the second piston and the accumulator piston towards the respective first ends of the first reservoir, the second reservoir and the accumulator chamber;

means for preventing fluid flow from the accumulator chamber into either of the first and second reservoirs so that when the first piston is driven towards the first end of the first reservoir by the stem, liquid in the first reservoir flows into the accumulator chamber so to tend to force the accumulator piston towards the second end of the accumulator chamber;

a pharmaceutical delivery head; and means for selectively fluidly coupling the accumulator chamber to the pharmaceutical delivery head so that when fluidly connected, any liquid in the accumulator chamber can be forced through the fluidly coupling means and to the pharmaceutical delivery head by driving the accumulator piston towards the first end of the accumulator chamber by the stem.

23. A variable ratio, liquid pharmaceutical dispensing syringe comprising:

first and second pistons;

an accumulator piston;

first and second variable volume reservoirs containing first and second liquids, wherein the first and second variable volume reservoirs are elongate with generally constant cross-sectional shapes, and the first and second variable volume reservoirs are partially defined by the first and second pistons;

a variable volume accumulator chamber, wherein the accumulator chamber is partially defined by the accumulator piston housed within the accumulator chamber;

means for permitting fluid flow from the first and second reservoirs into the accumulator chamber while preventing backflow;

a flowable material liquid delivery head including a hollow hypodermic needle;

means for fluidly coupling the hypodermic needle to the accumulator chamber;

means for forcing the first and second liquids form the first and second reservoirs to the accumulator chamber via the fluid flow permitting means, so that selected amounts of the first and second liquids are forced into the accumulator chamber to create a liquid mixture therein, the forcing means including a stem engageable with the first and second pistons; and means for expulsing the liquid mixture from the accumulator chamber through the delivery head via the fluidly coupling means, the expulsing means including the accumulator piston.

24. The system of claim 23 wherein the expulsing means includes said stem.

* * * * *